US012337182B2

(12) United States Patent
Esteller

(10) Patent No.: US 12,337,182 B2
(45) Date of Patent: *Jun. 24, 2025

(54) CLOSED LOOP CONTROL IN SPINAL CORD STIMULATION THERAPY WITH NON-DETECTABLE NEURAL RESPONSES

(71) Applicant: Boston Scientific Neuromodulation Corporation, Valencia, CA (US)

(72) Inventor: Rosana Esteller, Santa Clarita, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 77 days.

This patent is subject to a terminal disclaimer.

(21) Appl. No.: 18/466,399

(22) Filed: Sep. 13, 2023

(65) Prior Publication Data

US 2023/0414947 A1 Dec. 28, 2023

Related U.S. Application Data

(63) Continuation of application No. 17/137,141, filed on Dec. 29, 2020, now Pat. No. 11,794,016.

(60) Provisional application No. 62/976,800, filed on Feb. 14, 2020.

(51) Int. Cl.
*A61N 1/36* (2006.01)
*A61B 5/311* (2021.01)
*A61B 5/388* (2021.01)

(52) U.S. Cl.
CPC .......... *A61N 1/36139* (2013.01); *A61B 5/311* (2021.01); *A61B 5/388* (2021.01); *A61N 1/36062* (2017.08); *A61B 2562/0219* (2013.01)

(58) Field of Classification Search
CPC ................ A61N 1/36062; A61N 1/36139
See application file for complete search history.

(56) References Cited

U.S. PATENT DOCUMENTS

| 6,163,724 | A | 12/2000 | Hemming et al. |
|---|---|---|---|
| 6,181,969 | B1 | 1/2001 | Gord |
| 6,516,227 | B1 | 2/2003 | Meadows et al. |
| 8,190,258 | B2 | 5/2012 | Armstrong |
| 8,606,362 | B2 | 12/2013 | He et al. |

(Continued)

FOREIGN PATENT DOCUMENTS

| WO | 2012/088482 | 6/2012 |
|---|---|---|
| WO | 2018/080753 | 5/2018 |
| WO | 2020/251899 | 12/2020 |

OTHER PUBLICATIONS

International Search Report and Written Opinion regarding corresponding PCT Application No. PCT/US2020/067370, mailed Mar. 29, 2021.

*Primary Examiner* — Alyssa M Alter
(74) *Attorney, Agent, or Firm* — Lewis & Reese, PLLC

(57) ABSTRACT

Methods and systems for providing closed loop control of stimulation provided by an implantable stimulator device are disclosed herein. The disclosed methods and systems use a neural feature prediction model to predict a neural feature, which is used as a feedback control variable for adjusting stimulation. The predicted neural feature is determined based on one or more signals from an accelerometer configured in contact with the patient. The disclosed methods and systems can be used to provide closed loop feedback in situations, such as sub-perception therapy, when neural features cannot be readily directly measured.

20 Claims, 7 Drawing Sheets

(56) References Cited

U.S. PATENT DOCUMENTS

| | | |
|---|---|---|
| 8,620,436 B2 | 12/2013 | Parramon et al. |
| 9,259,574 B2 | 2/2016 | Aghassian et al. |
| 10,406,368 B2 | 9/2019 | Hershey et al. |
| 11,794,016 B2 * | 10/2023 | Esteller .................. A61B 5/311 |
| 2007/0208394 A1 | 9/2007 | King et al. |
| 2008/0071324 A1 | 3/2008 | Miesel et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2015/0080982 A1 | 3/2015 | Funderburk |
| 2015/0157861 A1 | 6/2015 | Aghassian |
| 2015/0231402 A1 | 8/2015 | Aghassian |
| 2015/0360038 A1 | 12/2015 | Zottola et al. |
| 2018/0071520 A1 | 3/2018 | Weerakoon et al. |
| 2018/0071527 A1 | 3/2018 | Feldman et al. |
| 2018/0117318 A1 | 5/2018 | Milekovic et al. |
| 2018/0140831 A1 | 5/2018 | Feldman et al. |
| 2019/0070418 A1 | 3/2019 | Hincapie Ordonez et al. |
| 2019/0076645 A1 | 3/2019 | Bower et al. |
| 2019/0076659 A1 | 3/2019 | Steinke et al. |
| 2019/0083796 A1 | 3/2019 | Weerakoon et al. |
| 2019/0099602 A1 | 4/2019 | Esteller et al. |
| 2019/0099606 A1 | 4/2019 | Shah et al. |
| 2019/0175915 A1 | 6/2019 | Brill et al. |
| 2019/0209844 A1 | 7/2019 | Esteller et al. |
| 2019/0275331 A1 | 9/2019 | Zhu |
| 2019/0290900 A1 | 9/2019 | Esteller et al. |
| 2019/0299006 A1 | 10/2019 | Marnfeldt |
| 2019/0366094 A1 | 12/2019 | Esteller et al. |
| 2020/0147393 A1 | 5/2020 | Zhang et al. |
| 2020/0155019 A1 | 5/2020 | Esteller et al. |
| 2020/0305744 A1 | 10/2020 | Weerakoon et al. |
| 2020/0305745 A1 | 10/2020 | Wagenbach et al. |
| 2022/0233866 A1 | 7/2022 | Gururaj et al. |
| 2022/0347479 A1 | 11/2022 | Esteller et al. |

\* cited by examiner

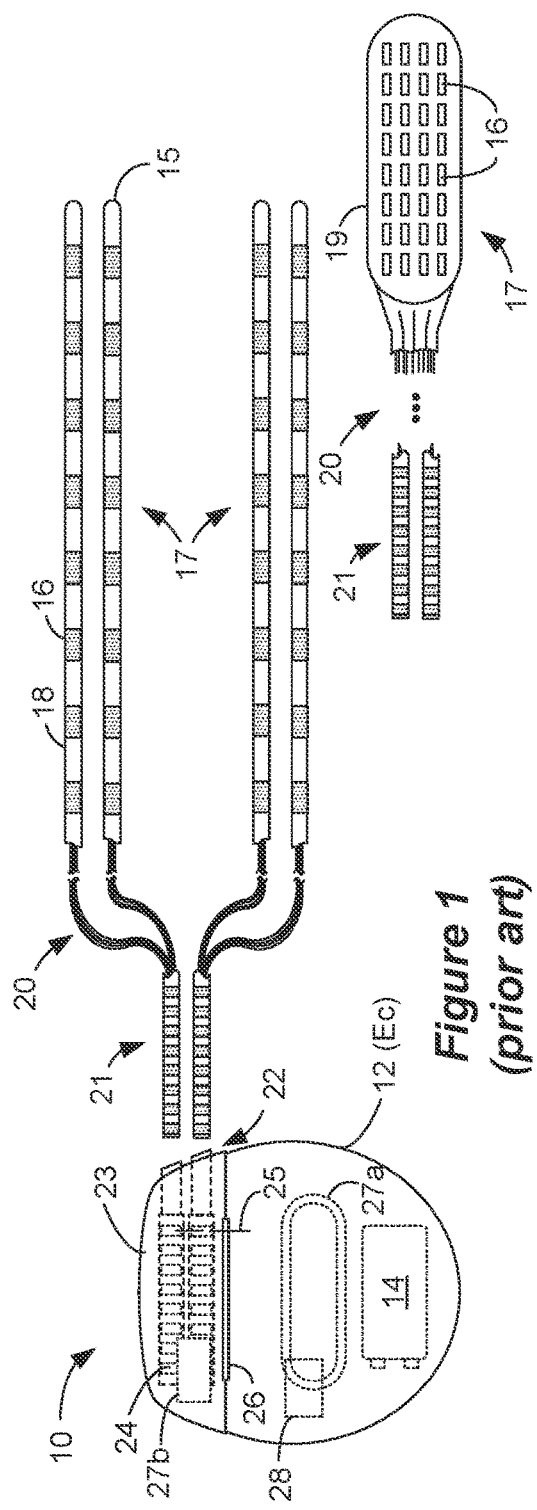
*Figure 1 (prior art)*
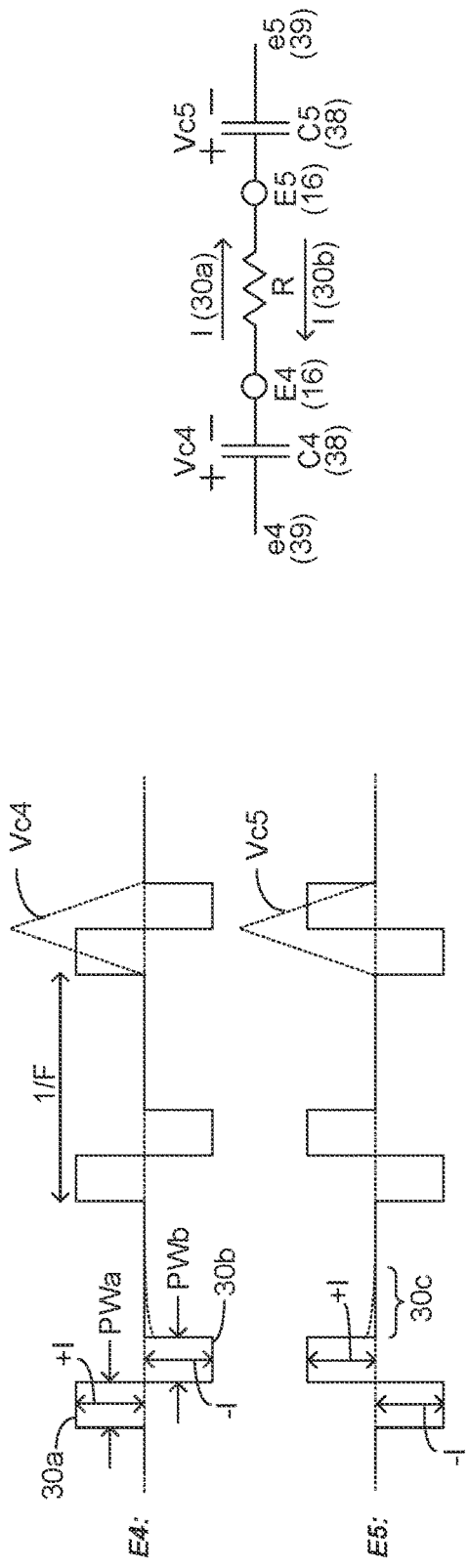
*Figure 2A (prior art)*
*Figure 2B (prior art)*

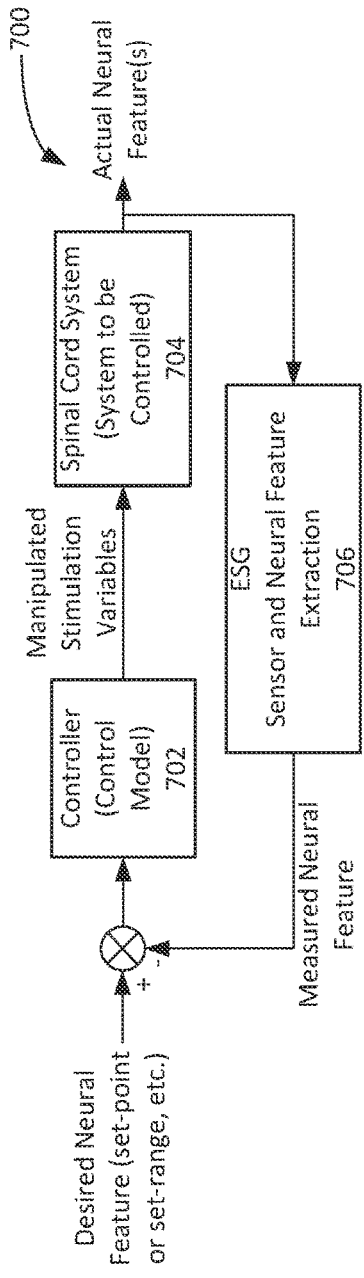

*Figure 7*

$$\hat{Y}_k = X \cdot A \qquad \text{Eq. 802}$$

$$A = (X^T X)^{-1} X^T Y_K \qquad \text{Eq. 804}$$

$$\begin{bmatrix} y_1 \\ y_2 \\ \vdots \\ y_n \end{bmatrix} = \begin{bmatrix} 1 & x_{11} & x_{12} & x_{13} & x_{14} & \cdots & x_{1p} \\ 1 & x_{21} & x_{22} & x_{23} & x_{24} & \cdots & x_{2p} \\ \vdots & \vdots & \vdots & \vdots & \vdots & & \vdots \\ 1 & x_{n1} & x_{n2} & x_{n3} & x_{n4} & \cdots & x_{np} \end{bmatrix} \cdot \begin{bmatrix} a_0 \\ a_1 \\ \vdots \\ a_p \end{bmatrix} \qquad \text{Eq. 806}$$

$Y_K \qquad X \qquad A$

*Figure 8*

CLOSED LOOP CONTROL IN SPINAL CORD STIMULATION THERAPY WITH NON-DETECTABLE NEURAL RESPONSES

CROSS REFERENCE TO RELATED APPLICATIONS

This is a continuation of U.S. patent application Ser. No. 17/137,141, filed Dec. 29, 2020, which is a non-provisional application of U.S. Provisional Patent Application Ser. No. 62/976,800, filed Feb. 14, 2020. Priority is claimed to these applications, and they are incorporated by reference in their entireties.

FIELD OF THE INVENTION

This application relates to Implantable Medical Devices (IMDs), and more specifically sensing signals in an implantable stimulator device.

INTRODUCTION

Implantable neurostimulator devices are implantable medical devices (IMDs) that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described for example in U.S. Patent Application Publication 2019/0175915. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +I to the tissue. Electrode E5 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIG. 2A), and during the first phase 30a in which electrodes E4 and E5 are selected as an anode and cathode respectively, PDAC $40_4$ and NDAC $42_5$ are activated and digitally programmed to produce the desired current, I, with the correct timing (e.g., in accordance with the prescribed frequency F and pulse width PWa). During the second phase 30b (PWb), PDAC $40_5$ and NDAC $42_4$ would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allow one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27a and/or 27b), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Although not shown, circuitry in the IPG 10 including the stimulation circuitry 28 can also be included in an External Trial Stimulator (ETS) device which is used to mimic operation of the IPG during a trial period and prior to the IPG 10's implantation. An ETS device is typically used after the electrode array 17 has been implanted in the patient. The proximal ends of the leads in the electrode array 17 pass through an incision in the patient and are connected to the externally-worn ETS, thus allowing the ETS to provide stimulation to the patient during the trial period. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30a followed thereafter by a second phase 30b of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30b of each pulse (Vc4=Vc5=0V), the first and second phases 30a and 30b are preferably charged balanced at each electrode, with the phases comprising an equal amount of charge but of the opposite polarity. In the example shown, such charge balancing is achieved by using the same pulse width (PWa=PWb) and the same amplitude ($|+I|=|-I|$) for each of the pulse phases 30a and 30b. However, the pulse phases 30a and 30b may also be charged balance if the product of the amplitude and pulse widths of the two phases 30a and 30b are equal, as is known.

FIG. 3 shows that stimulation circuitry 28 can include passive recovery switches 41i, which are described further in U.S. Patent Application Publications 2018/0071527 and 2018/0140831. Passive recovery switches 41i may be attached to each of the electrode nodes 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced. Passive charge recovery typically occurs during at least a portion 30c (FIG. 2A) of the quiet periods between the pulses by closing passive recovery switches 41i. As shown in FIG. 3, the other end of the switches 41i not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30c in FIG. 2A, which may be positive or negative depending on whether pulse phase 30a or 30b has a predominance of charge at a given electrode.

FIG. 4 shows various external devices that can wirelessly communicate data with the IPG 10 and/or the ETS 80, including a patient, hand-held external controller 45, and a clinician programmer 50. Both of devices 45 and 50 can be used to wirelessly send a stimulation program to the IPG 10 or ETS 80—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 80 is currently executing. Devices 45 and 50 may also receive information from the IPG 10 or ETS 80, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 80, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 80. For example, the external controller 45 can have a near-field magnetic-induction coil antenna 47a capable of wirelessly communicating with the coil antenna 27a or 42a in the IPG 10 or ETS 80. The external controller 45 can also have a far-field RF antenna 47b capable of wirelessly communicating with the RF antenna 27b or 42b in the IPG 10 or ETS 80.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 80.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 to communicate with the IPG 10 or ETS 80 can depend on the type of antennas included in those devices. If the patient's IPG 10 or ETS 80 includes a coil antenna 27a or 82a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 80. If the IPG 10 or ETS 80 includes an RF antenna 27b or 82b, the wand 54, the computing device 51, or both, can likewise include an RF antenna 56b to establish communication with the IPG 10 or ETS 80 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 80, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

While GUI 64 is shown as operating in the clinician programmer 50, the user interface of the external controller 45 may provide similar functionality as the external controller 45 may have similar controller circuitry, software, etc.

SUMMARY

Disclosed herein is method of operating an implantable stimulator device configured for implantation in a patient, the stimulator device comprising a plurality of electrodes configured to contact the patient's tissue, the method comprising: providing stimulation at at least one of the electrodes; receiving one or more accelerometer signals from an accelerometer attached to the patient; determining at least one predicted neural feature from the at least one accelerometer signal using a prediction model that is configured to predict one or more neural features based on one or more accelerometer signals, wherein the one or more neural features are indicative of a neural response to the stimulation; and using the determined at least one predicted neural feature to adjust the stimulation. According to some embodiments, using the at least one predicted neural feature to adjust the stimulation comprises adjusting the stimulation to maintain the at least one predicted neural feature within a set-range of values. According to some embodiments, using the at least one predicted neural feature to adjust the stimulation comprises adjusting the stimulation to maintain the at least one predicted neural feature relative to a set-point. According to some embodiments, using the at least one predicted neural feature to adjust the stimulation comprises adjusting the stimulation to maintain the at least one predicted neural feature comprises using a control model to adjust stimulation settings. According to some embodiments, the control model is selected from the group consisting of Kalman filtering algorithms, heuristic algorithms, simple threshold model, and proportional-integral-derivative (PID) controller models. According to some embodiments, the stimulation is below a perception threshold for the patient. According to some embodiments, the method further comprises determining the prediction model. According to some embodiments, determining the prediction model comprises: providing supra-threshold stimulation to the patient; recording an electrospinogram (ESG) of the patient while receiving the one or more accelerometer signals; processing the ESG to extract an evoked compound action potential (ECAP) signal from the ESG; determining one or more features of the ECAP signal; and determining a mathematical expression that expresses the one or more features of the ECAP signal as a function of the one or more accelerometer signals. According to some embodiments, the mathematical expression comprises a linear regression. According to some embodiments, the mathematical expression comprises a fitting algorithm selected from the group consisting of support vector machines (SVM), decision trees, and neural networks. According to some embodiments, the prediction model is configured to predict one or more neural features based on one or more accelerometer signals and one or more stimulation parameters. According to some embodiments, the accelerometer is configured as a component of the implantable stimulator device. According to some embodiments, the accelerometer is worn externally by the patient.

Also disclosed herein is n implantable medical device (IMD) comprising and implantable pulse generator (IPG) and a plurality of electrodes configured to contact a patient's tissue, wherein the IPG is configured to: provide stimulation at at least one of the electrodes; receive at least one accelerometer signal from an accelerometer attached to the patient; determine at least one predicted neural feature from the determined at least one accelerometer signal using a prediction model that is configured to predict one or more neural features based on one or more accelerometer signals, wherein the one or more neural features are indicative of a neural response to the stimulation; and use the determined at least one predicted neural feature to adjust the stimulation. According to some embodiments, using the at least one predicted neural feature to adjust the stimulation comprises adjusting the stimulation to maintain the at least one predicted neural feature within a set-range of values. According to some embodiments, using the at least one predicted neural feature to adjust the stimulation comprises adjusting the stimulation to maintain the at least one predicted neural feature relative to a set-point. According to some embodiments, using the at least one predicted neural feature to adjust the stimulation comprises adjusting the stimulation to maintain the at least one predicted neural feature comprises using a control model to adjust stimulation settings. According to some embodiments, the control model is selected from the group consisting of Kalman filtering algorithms, heuristic algorithms, simple threshold model, and proportional-integral-derivative (PID) controller models. According to some embodiments, the stimulation is below a perception threshold for the patient. According to some embodiments, the prediction model determines the at least one predicted neural feature as a weighted linear combination of a plurality of accelerometer signals. According to some embodiments, the prediction model is programmed into a control circuitry of the IPG. According to some embodiments, the IMD comprises a Spinal Cord Stimulator device. According to some embodiments, the prediction model is configured to predict one or more neural features based on one or more accelerometer signals and one or more stimulation parameters. According to some embodiments, the accelerometer is configured as a component of the IMD. According to some embodiments, the accelerometer is worn externally by the patient.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 1 shows an Implantable Pulse Generator (IPG), in accordance with the prior art.

FIGS. 2A and 2B show an example of stimulation pulses producible by the IPG, in accordance with the prior art.

FIG. 7 shows a control system for using a measured neural feature for controlling stimulation.

FIG. 8 shows the development of a prediction model.

DETAILED DESCRIPTION

Figure 5:
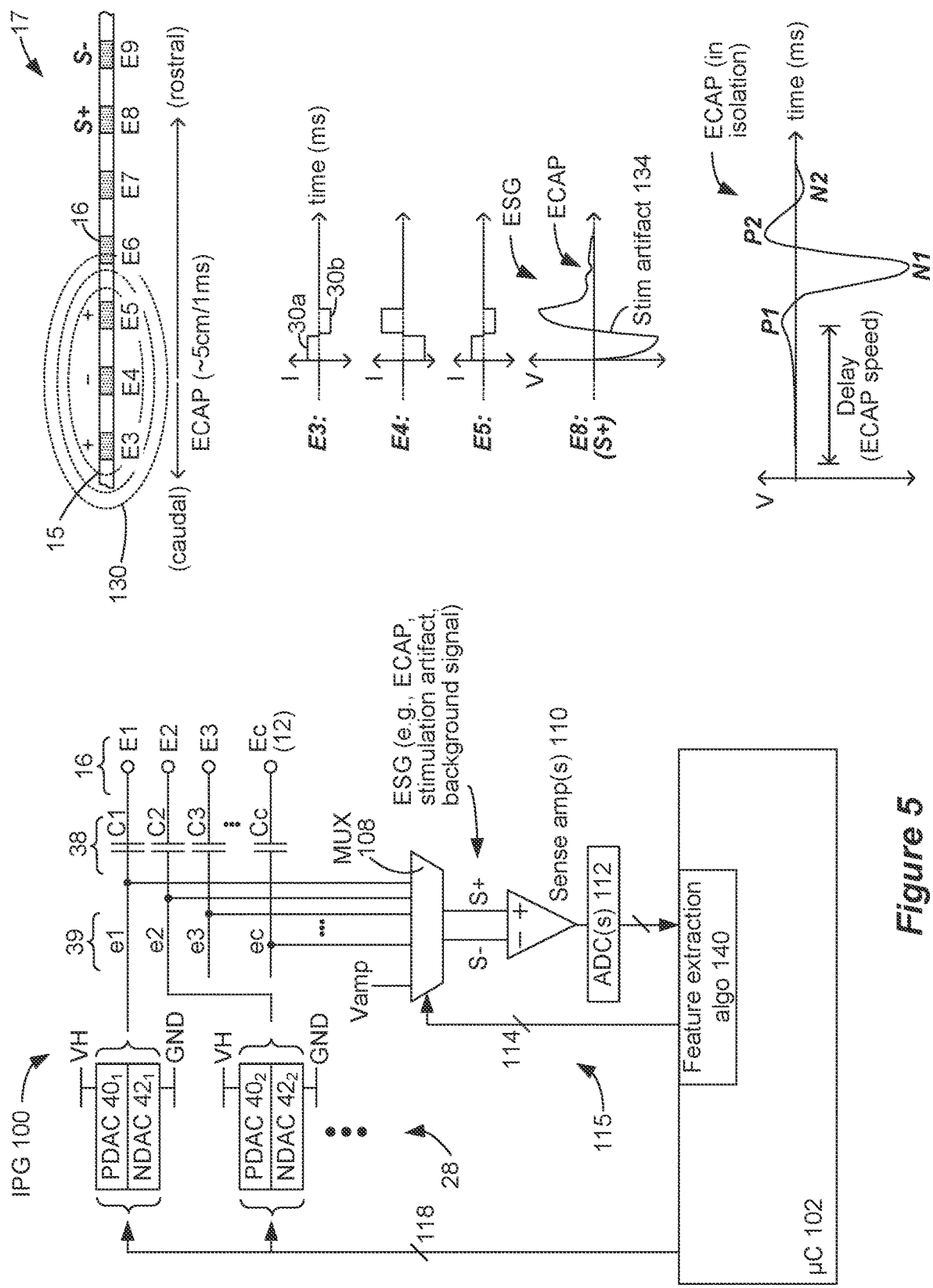
FIG. 5 shows an improved IPG having stimulation capability and the ability to sense an ElectroSpinoGram (ESG) signal which may include Evoked Compound Action Potentials (ECAPs) caused by the simulation.

An increasingly interesting development in pulse generator systems, and in Spinal Cord Stimulator (SCS) pulse generator systems specifically, is the addition of sensing capability to complement the stimulation that such systems provide. FIG. 5 shows an IPG 100 that includes stimulation and sensing functionality. (An ETS as described earlier could also include stimulation and sensing capabilities, and the circuitry shown in FIG. 5, but this disclosure focuses on description in an IPG for simplicity).

For example, it can be beneficial to sense a neural response in neural tissue that has received stimulation from the IPG 100. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in isolation in FIG. 5, and comprises a number of peaks that are conventionally labeled with P for positive peaks and N for negative peaks, with P1 comprising a first positive peak, N1 a first negative peak, P2 a second positive peak, and so on. Note that not all ECAPs will have the exact shape and number of peaks as illustrated in FIG. 5, because an ECAP's shape is a function of the number and types of neural elements that are recruited and that are involved in its conduction. An ECAP is generally a small signal, and may have a peak-to-peak amplitude on the order of hundreds of microVolts or more.

FIG. 5 also shows an electrode array 17 comprising (in this example) a single percutaneous lead 15, and shows use of electrodes E3, E4 and E5 to produce pulses in a tripolar mode of stimulation, with (during the first phase 30a) E3 and E5 comprising anodes and E4 a cathode. Other electrode arrangements (e.g., bipoles, etc.) could be used as well. Such stimulation produces an electric field 130 in a volume of the patient's tissue centered around the selected electrodes.

Some of the neural fibers within the electric field 130 will be recruited and fire, particularly those proximate to the cathodic electrode E4, forming ECAPs which can travel both rostrally toward the brain and caudally away from the brain. The ECAPs pass through the spinal cord by neural conduction with a speed which is dependent on the neural fibers involved in the conduction. In one example, the ECAP may move at a speed of about 5 cm/1 ms. U.S. Patent Application Publication 2020/0155019, describes a lead that can be useful in the detection of ECAPs.

ECAPs can be sensed at one or more sensing electrodes which can be selected from the electrodes 16 in the electrode array 17. Sensing preferably occurs differentially, with one electrode (e.g., S+, E8) used for sensing and another (e.g., S−, E9) used as a reference. This could also be flipped, with E8 providing the reference (S−) for sensing at electrode E9 (S+). Although not shown, the case electrode Ec (12) can also be used as a sensing reference electrode S−. Sensing reference S− could also comprise a fixed voltage provided by the IPG 100 (e.g., Vamp, discussed below), such as ground, in which case sensing would be said to be single-ended instead of differential.

Figure 4:
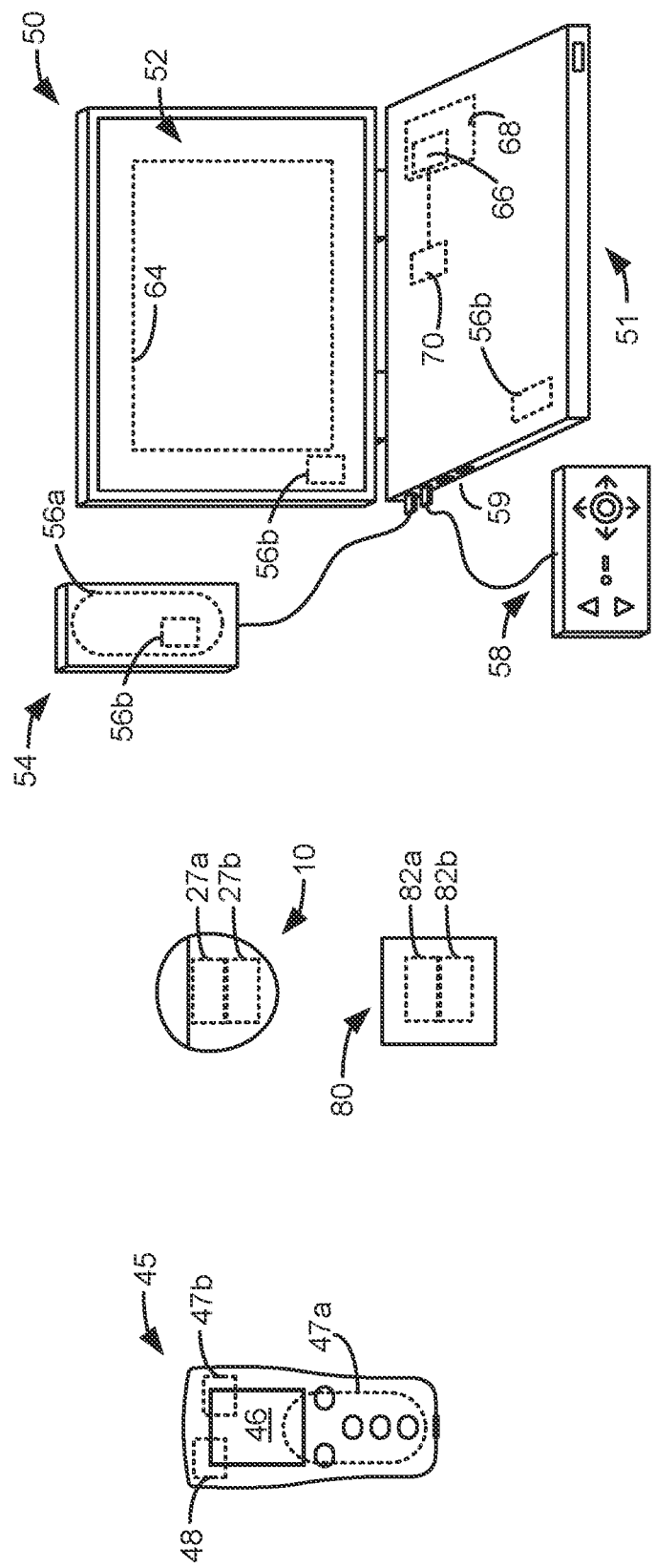
FIG. 4 shows external devices able to communicate with the IPG, in accordance with the prior art.

The waveform appearing at sensing electrode E8 (S+) is shown in FIG. 5, which includes a stimulation artifact 134 as well as an ECAP. The stimulation artifact 134 comprises a voltage that is formed in the tissue as a result of the stimulation, i.e., as a result of the electric field 130 that the stimulation creates in the tissue. As described in U.S. Patent Application Publication 2019/0299006, the voltage in the tissue can vary between ground and the compliance voltage VH used to power the DACs, and so the stimulation artifact 134 can be on the order of Volts, and therefore significantly higher than the magnitude of stimulation-induced ECAPs. Generally speaking, the waveform sensed at the sensing electrode may be referred to as an ElectroSpinoGram (ESG) signal, which comprises the ECAP, the stimulation artifact 134, and other background signals that may be produced by neural tissue even absent stimulation. Realize that the ESG signal as shown at the sensing electrode S+ in FIG. 4 is idealized. The figures in U.S. Patent Application Publication 2022/0323764, show actual recorded ESG traces.

The magnitudes of the stimulation artifact 134 and the ECAP at the sensing electrodes S+ and S− are dependent on many factors, such as the strength of the stimulation, and the distance of sensing electrodes from the stimulation. ECAPs tend to decrease in magnitude at increasing stimulation-to-sensing distances because they disperse in the tissue. Stimulation artifacts 134 also decrease in magnitude at increasing stimulation-to-sensing distances because the electric field 130 is weaker at further distances. Note that the stimulation artifact 134 is also generally larger during the provision of the pulses, although it may still be present even after the pulse (i.e., the last phase 30b of the pulse) has ceased, due to the capacitive nature of the tissue or the capacitive nature of the driving circuitry (i.e., the DACs). As a result, the electric field 130 may not dissipate immediately upon cessation of the pulse.

It can be useful to sense in the IPG 100 features of either or both of the ECAPs or stimulation artifact 134 contained within the sensed ESG signal, because such features can be used to useful ends. For example, ECAP features can be used to adjust the stimulation the IPG 100 provides. See, e.g., U.S. Pat. No. 10,406,368; U.S. Patent Application Publications 2019/0099602, 2019/0209844, 2019/0070418, 2020/0147393 and 2022/0347479. ECAP assessment can also be used to infer the types of neural elements or fibers that are recruited, which can in turn be used to adjust the stimulation to selectively stimulate such elements. See, e.g., U.S. Patent Application Publication 2019/0275331. Assessments of ECAP features can also be used to determine cardiovascular effects, such as a patient's heart rate. See, e.g., U.S. Patent Application Publication 2019/0290900. To the extent one wishes to assess features of an ECAP that are obscured by a stimulation artifact, U.S. Patent Application Publication 2019/0366094 discloses techniques that can used to extract ECAP features from the ESG signal. As discussed in some of these references, detected ECAPs can also be dependent on a patient's posture or activity, and therefor assessment of ECAP features can be used to infer a patient's posture, which may then in turn be used to adjust the stimulation that the IPG 100 provides.

It can also be useful to detect features of stimulation artifacts 134 in their own right. For example, U.S. Patent Application Publication 2022/0323764 describes that features of stimulation artifacts can be useful to determining patent posture or activity, which again may then in turn be used to adjust the stimulation that the IPG 100 provides.

FIG. 5 shows further details of the circuitry in an IPG 100 that can provide stimulation and sensing an ElectroSpino-Gram (ESG) signal. The IPG 100 includes control circuitry 102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

Figure 3:
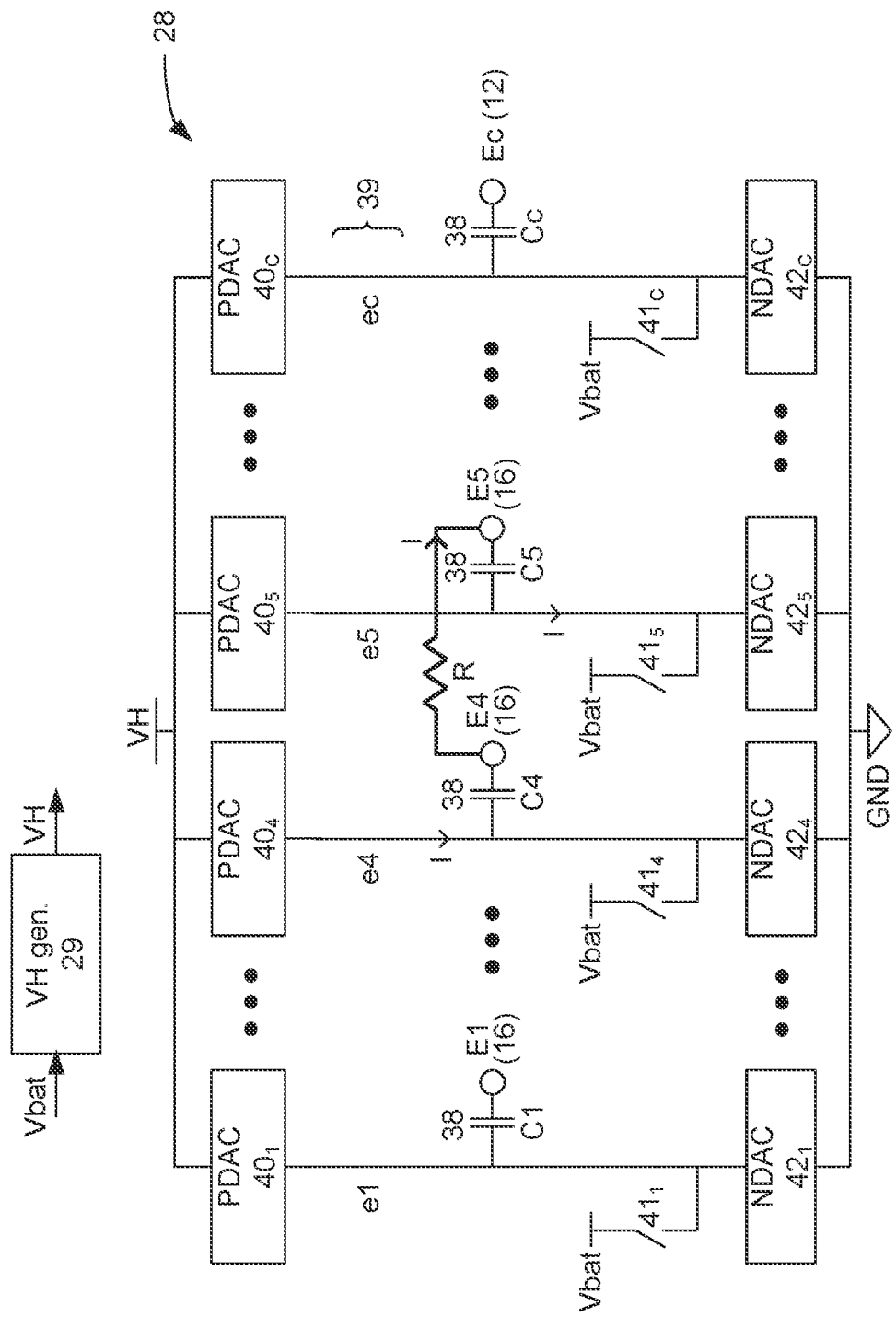
FIG. 3 shows stimulation circuitry useable in the IPG, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an feature extraction algorithm 140, described below) to one or more PDACs $40_i$ or NDACs $42_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present, but are not shown in FIG. 5 for simplicity.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 5, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S– to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the ESG signals being sensed (such as the ECAP and stimulation artifact) will still readily be sensed by the sense amp circuitry 110. In other examples, signals may be sensed directly at the electrodes 16 without passage through intervening capacitors 38.

As noted above, it is preferred to sense an ESG signal differentially, and in this regard, the sense amp circuitry 110 comprises a differential amplifier receiving the sensed signal S+ (e.g., E8) at its non-inverting input and the sensing reference S– (e.g., E9) at its inverting input. As one skilled in the art understands, the differential amplifier will subtract S– from S+ at its output, and so will cancel out any common mode voltage from both inputs. This can be useful for example when sensing ECAPs, as it may be useful to subtract the relatively large scale stimulation artifact 134 from the measurement (as much as possible) in this instance. That being said, note that differential sensing will not completely remove the stimulation artifact, because the voltages at the sensing electrodes S+ and S– will not be exactly the same. For one, each will be located at slightly different distances from the stimulation and hence will be at different locations in the electric field 130. Thus, the stimulation artifact 134 can still be sensed even when differential sensing is used. Examples of sense amp circuitry 110, and manner in which such circuitry can be used, can be found in U.S. Patent Application Publications 2019/0299006, 2020/0305744, 2020/0305745 and 2022/0233866.

The digitized ESG signal from the ADC(s) 112—inclusive of any detected ECAPs and stimulation artifacts—is received at a feature extraction algorithm 140 programmed into the IPG's control circuitry 102. The feature extraction algorithm 140 analyzes the digitized sensed signals to determine one or more ECAP features, and one or more stimulation artifact features, as described for example in U.S. Patent Application Publication 2022/0323764. Such features may generally indicate the size and shape of the relevant signals, but may also be indicative of other factors (like ECAP conduction speed). One skilled in the art will understand that the feature extraction algorithm 140 can comprise instructions that can be stored on non-transitory machine-readable media, such as magnetic, optical, or solid-state memories within the IPG 100 (e.g., stored in association with control circuitry 102).

For example, the feature extraction algorithm 140 can determine one or more ECAP features, which may include but are not limited to:

- a height of any peak (e.g., N1);
- a peak-to-peak height between any two peaks (such as from N1 to P2);
- a ratio of peak heights (e.g., N1/P2);
- a peak width of any peak (e.g., the full-width half-maximum of N1);
- an area or energy under any peak;
- a total area or energy comprising the area or energy under positive peaks with the area or energy under negative peaks subtracted or added;
- a length of any portion of the curve of the ECAP (e.g., the length of the curve from P1 to N2);
- any time defining the duration of at least a portion of the ECAP (e.g., the time from P1 to N2);
- a time delay from stimulation to issuance of the ECAP, which is indicative of the neural conduction speed of the ECAP, which can be different in different types of neural tissues;
- a conduction speed of the ECAP, which can be determined by sensing the ECAP as it moves past different sensing electrodes;
- a rate of variation of any of the previous features, i.e., how such features change over time;
- a power (or energy) determined in a specified frequency band (e.g., delta, alpha, beta, gamma, etc.) determined in a specified time window (for example, a time window that overlaps the neural response, the stimulation artifact, etc.);
- any mathematical combination or function of these variables.

Such ECAP features may be approximated by the feature extraction algorithm 140. For example, the area under the curve may comprise a sum of the absolute value of the sensed digital samples over a specified time interval. Similarly, curve length may comprise the sum of the absolute value of the difference of consecutive sensed digital samples over a specified time interval. ECAP features may also be determined within particular time intervals, which intervals may be referenced to the start of simulation, or referenced from within the ECAP signal itself (e.g., referenced to peak N1 for example).

In this disclosure, ECAP features, as described above, are also referred to as neural features. This is because such ECAP features contain information relating to how various neural elements are excited/recruited during stimulation, and in addition, how these neural elements spontaneously fired producing spontaneous neural responses as well.

The feature extraction algorithm 140 can also determine one or more stimulation artifact features, which may be similar to the ECAP features just described, but which may also be different to account for the stimulation artifact 134's different shape. Determined stimulation artifact features may include but are not limited to:

- a height of any peak;
- a peak-to-peak height between any two peaks;
- a ratio of peak heights;
- an area or energy under any peak;
- a total area or energy comprising the area or energy under positive peaks with the area or energy under negative peaks subtracted or added;
- a length of any portion of the curve of the stimulation artifact;
- any time defining the duration of at least a portion of the stimulation artifact;
- a rate of variation of any of the previous features, i.e., how such features change over time;
- a power (or energy) determined in a specified frequency band (e.g., delta, alpha, beta, gamma, etc.) determined in a specified time window (for example, a time window that overlaps the neural response, the stimulation artifact, etc.);

any mathematical combination or function of these variables.

Again, such stimulation artifact features may be approximated by the feature extraction algorithm 140, and may be determined with respect to particular time intervals, which intervals may be referenced to the start or end of simulation, or referenced from within the stimulation artifact signal itself (e.g., referenced to a particular peak).

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus 118. This is explained further in some of the U.S. patent documents cited above.

This disclosure relates to methods and systems that use measured or estimated neural features as feedback for adjusting and maintaining stimulation therapy (e.g., SCS therapy). The disclosed methods and systems are particularly useful during the provision of sub-perception therapy. Sub-perception (also known as sub-threshold or paresthesia-free) therapy involves providing stimulation that the patient does not readily perceive. With traditional paresthesia (or supra-threshold) therapy, patients typically perceive sensations, such as tingling sensations, that accompany stimulation. Such sensations are referred to as paresthesia. Sub-perception therapy involves providing stimulation with lower stimulation amplitudes that do not evoke paresthesia and correspond to amplitudes below perception threshold or at sub-threshold stimulation amplitudes.

During stimulation at, or below the patient's perception threshold (the stimulation amplitude at which the patient begins to experience paresthesia) ECAPs may not be readily detectable and are, therefore, not available as feedback for adjusting/maintaining stimulation therapy. In other words, if an ECAP is not readily detectable, then it is impossible to extract a usable neural feature from it. The disclosed methods and systems allow neural features to be estimated (based on modeling) even when ECAPs are not detectable, which estimated neural features can be used for feedback control.

According to the disclosed methods and systems, accelerometer signals combined with one or more stimulation parameter values are used to estimate neural features in situations when ECAP signals are not readily detectable. The patient is fitted with a wearable or an implanted accelerometer. The accelerometer may be an integral component of the IMD. For example, the accelerometer may be contained within the IPG 10 or could be configured within the leads 15 (FIG. 1). Alternatively, the accelerometer may be attached externally to the patient, for example, by a strap around the patient's torso.

As will be appreciated by those of skill in the art, an accelerometer comprises transducers that produce signals indicative of the accelerometer's orientation with respect to the earth's gravitational acceleration. For example, the accelerometer may produce electrical signals corresponding to the x, y, and z directions that are indicative of the accelerometer's orientation. Other coordinate systems (e.g., cylindrical coordinates) may be used, but Cartesian coordinates are considered in this disclosure.

When the patient is fitted with an accelerometer (either internally or externally), the accelerometer signals depend on the patient's posture and activity. The patient's posture and activity influence the distance between the stimulating electrodes and the patient's neural tissue (e.g., the spinal cord). The inventor has discovered that the accelerometer signals can be correlated with neural features observed during stimulation independent of posture. The disclosed methods and systems use ECAP signals and accelerometer signals measured during supra-threshold (paresthesia) stimulation to create a prediction model, which is a function that relates the ECAP and accelerometer measurements. Then, when sub-perception stimulation is used (with no measurable ECAP), the prediction model and sensed accelerometer measurements are used as feedback for adjusting/ maintaining therapy.

Figure 6:
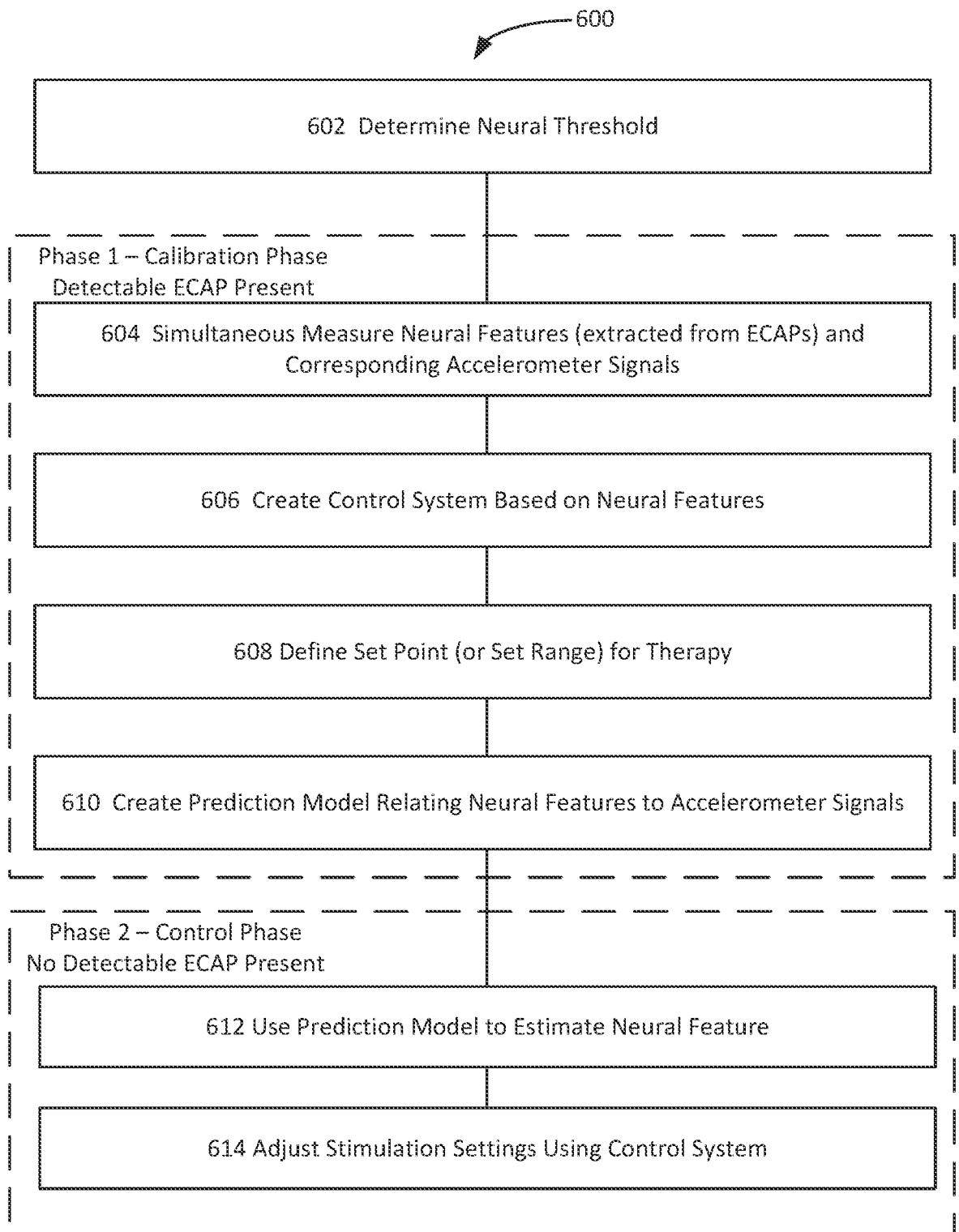
FIG. 6 shows a workflow for determining a prediction model and using predicted neural features as the feedback controlled variable for controlling stimulation.

FIG. 6 illustrates an example workflow 600 for the disclosed method. The workflow comprises two phases— Phase 1 (Calibration Phase), which is performed using electrical stimulation that is above the perception threshold and which evokes measurable/detectable ECAP signals, and Phase 2 (Control Phase), which is performed when no ECAP signals are detectable. Note that the steps of the exemplary workflow 600 may occur in a different order than illustrated. But the Phase 1 steps are typically performed together, and the Phase 2 steps are typically performed together.

Step 602 of the workflow 600 comprises determining a neural threshold for the patient. The "neural threshold" (as the term is used herein) refers to the lowest stimulation intensity at which ECAP signals are detectable. The neural threshold may be an "extracted neural threshold," meaning that it corresponds to the lowest stimulation intensity at which an ECAP signal (or ECAP features) may be extracted from the ESG using extraction techniques such as signal averaging or other signal processing (such as described in U.S. Patent Application Publication 2019/0366094, recited above). At step 602 (or at any time during the workflow) other stimulation thresholds may be determined and saved, such as the patient's perception threshold (the minimum stimulation intensity at which the patient perceives the stimulation), discomfort threshold (the minimum stimulation intensity that first causes discomfort), and/or maximum comfort threshold (the maximum stimulation intensity that is strong but still comfortable to the patient). Such other threshold values may inform the setting of stimulation setpoints, as described below.

Once the patient's neural threshold is determined, the remaining Phase 1 steps are performed using stimulation intensities that are above the neural threshold such that ECAP signals and features are measurable. At step 604, a plurality of measurements is made of one or more ECAP features (neural features). According to some embodiments, ESG data is collected with stimulation that is above the neural threshold and with constant stimulation parameters (e.g., amplitude, frequency, pulse width, etc.). The patient may be instructed to perform a variety of tasks (e.g., laugh, cough, walk, march in place, etc.) and/or assume a variety of postures (e.g., standing, sitting, supine, prone, etc.) while the stimulation is applied and ESG data is obtained and simultaneous recording of the accelerometer signals is conducted. Such a posture/activity routine provides different spinal cord states, i.e., provides different distances and/or orientations of the stimulation/sensing electrodes with respect to the spinal cord. According to some embodiments, the process of acquiring ESG data with variations in activity/posture may be repeated with different stimulation settings. The acquired ESGs can be analyzed to extract a one or more neural features (ECAP features). Examples of neural features (ECAP features) are described above (e.g., peak height (intensity), peak-to-peak distance, area under the curve, curve length, etc.). Multiple features may be extracted, and features may be extracted on multiple channels (i.e., electrode channels) of the electrode leads.

For this example, assume that one neural feature (e.g., the ECAP curve length) is determined. Multiple observations of the neural feature are collected as the patient moves through the posture/task routine. Each observed instance of the neural feature is associated with accelerometer signals (e.g., x, y, and z signals) that correspond to the accelerometer state at the time the observation was made. Each observed instance of the neural feature is also associated with one or more values of the stimulation parameters (e.g., stimulation intensity, pulse width, frequency, etc.) that were used when the observation was made. This correlation of the observed instances of the neural feature with the accelerometer signals and stimulation parameters will be used to construct the prediction model, as described below.

According to some embodiments, when ECAPs are extracted, discrimination criteria may be used to ensure that only reliable ECAP signals are considered. For example, candidate ECAP signals with widths that fluctuate wildly may be excluded.

At step 606, the extracted neural feature(s) can be used to create a control system for controlling stimulation therapy using the neural feature(s) as a feedback variable. According to some embodiments, this involves determining one or more set-points, set-ranges, or maximum threshold values for the neural feature(s) that correspond to comfortable and effective stimulation therapy. These set-point/set-ranges may be determined using supra-threshold (paresthesia) stimulation settings for a selected posture or across multiple postures (step 608). The control system is then used to adjust the stimulation settings to maintain the neural feature(s) with respect to the set-point/set-range.

FIG. 7 illustrates a control diagram of a control system 700 for adjusting stimulation based on the extracted neural feature(s). The determined set-point or set-range that corresponds to desirable therapy is referred to as the "desired neural feature" in FIG. 7. The control system 700 uses a controller (i.e., control model) 702 that seeks to adjust the stimulation setting provided to the spinal cord system 704, causing the spinal cord system to express actual neural features that matches the desired neural features, thereby arriving at the comfortable and effective therapy. The controller 702 can be essentially any algorithm that is configured to adjust the stimulation settings to minimize the difference between the measured neural feature extracted from the sensed ESG (as measured by the sensing electrodes 706) and the desired neural feature. Examples of features that can be extracted from the ESG include the range, area under the curve (AUC), curve length (CL), power in a frequency band (from the ECAP, artifact, or spontaneous neural responses). Examples of control models include such algorithms as Kalman filter algorithms, heuristic control algorithms, simple threshold control model, and proportional-integral-derivative (PID) controller models. The control model may also be a hybrid of any of these methods. Thus, the control system 700 can provide closed-loop feedback control of stimulation to maintain therapy in situations when neural features can be extracted from readily measurable ECAP signals. However, since the control system 700 depends on the presence of a measurable ECAP signal it is not adequate for sub-perception therapy, when no usable ECAP signals are present. But the controller model 702 developed for the control system 700 can be adapted for sub-perception use, as described below.

Referring again to FIG. 6, at step 610 the extracted neural feature(s), the accelerometer signals, and one or more stimulation parameters are used to create a prediction model that is configured to predict a neural feature (when it cannot be measured) based on measured accelerometer signals and stimulation parameters. FIG. 8 illustrates a least mean square formulation for deriving such a model 800. Assume that predicted values of the neural feature $\hat{y}$ can be expressed as a vector ($\hat{Y}_k$), which is a product of a matrix (X) times a vector (A) (Eq. 802). The matrix X comprises accelerometer values and stimulation parameters paired to their corresponding neural features $y_i$ in vector ($\hat{Y}_k$), where i varies from 1 to n, and n is the total number of features extracted from the neural response in eq. 806. Vector A comprises regression coefficients that can be computed by using equation 804, where matrix X and vector $Y_k$ are known, and therefore, coefficients in vector A can be determined. Once the regression coefficients in A are determined, after computing them from equation 804, they can be used to solve for predicted $\hat{y}_i$ values as indicated in equation 806, based on the accelerometer signals and one or more stimulation parameters Eq. 804 shows the solution for vector A (the regression coefficients) based on a measured vector $Y_K$, which comprises actual observations of neural features y (e.g., as obtained as per Step 604 of FIG. 6) and the matrix X, which comprises the corresponding accelerometer signals and one or more stimulation parameters (Step 604 of FIG. 6). Eq. 806 shows the solution expressed in matrix form. The vector $Y_K$ comprises values for n observations of neural features $y_i$, extracted from the neural response at time k, determined using supra-perception stimulation as described in Step 604 (FIG. 6) above. In Eq. 806, $y_1$ is the observation of the first neural feature in vector $Y_k$ and each $x_{ij}$ is an accelerometer signal value or stimulation parameter value corresponding to that observation $y_1$. For example, $x_{11}$ may be the corresponding accelerometer x-axis signal, $x_{12}$ may be the corresponding accelerometer y-axis signal, $x_{13}$ may be the corresponding accelerometer z-axis signal, $x_{14}$ may be the corresponding stimulation amplitude, up to $x_{1p}$ which may be a further stimulation parameter or accelerometer value including a gyroscopic value.

The regression model 800 may be trained using data collected on a patient using supra-threshold (paresthesia) stimulation (i.e., with an ECAP present) to determine the values of the regression coefficients A, $a_0$–$a_p$. For example, the regression model may be trained on data collected on a patient during prescribed postural changes or a continuous recording. Cross-validation can be performed to control for overfitting. Once the $a_i$ values are determined, they can then be used to estimate a neural feature value y as a linear combination of the accelerometer signals and stimulation parameters, each weighted by its corresponding a value. This estimation model can be used to estimate a neural feature when the neural feature is not measurable. Other models that can be trained to relate a neural feature (ECAP feature) to accelerometer signals and stimulation parameters can also be used. Examples include other common fitting machine learning models such as support vector machines (SVM), decision trees, neural networks, etc.

Referring again to FIG. 6, the phase 1 (calibration) steps provide (1) a control model that is capable of controlling/maintaining stimulation therapy based on sensed neural features by maintaining the neural feature within a set-range or relative to a set-point, and (2) a prediction model that is capable of predicting one or more neural features (when they cannot be measured) based on measured accelerometer signals. The control model in step 1, can be one of several types of feedback controllers selected from a library containing multiple controller choices such as Kalman filter, heuristic thresholds, PID (proportional-derivative-integral)

controller, PD (proportional derivative), simple proportional, based adaptive threshold, etc. Any of these controllers, can operate using either a set-point, a set-range (upper and lower thresholds), a max-point (upper threshold), or stimulation intensity set-range at paresthesia settings. A set-point is considered a target neural feature value to be preserved during closed-loop control, determined using one or more constant postures(s) at high but comfortable stimulation settings. A max-point is a neural feature value corresponding to the maximum stimulation intensity that produces a comfortable or tolerable sensation. The phase 2 steps comprise using the prediction model to predict neural features in situations (such as sub-perception therapy) when ECAP signals are not detectable. During phase 2, stimulation is provided to the patient using sub-threshold stimulation parameters, and thus, no ECAP signal is detectable. At step 612, accelerometer signal values and stimulation parameters are used by the prediction model established as described above to predict the neural features.

Figure 9:
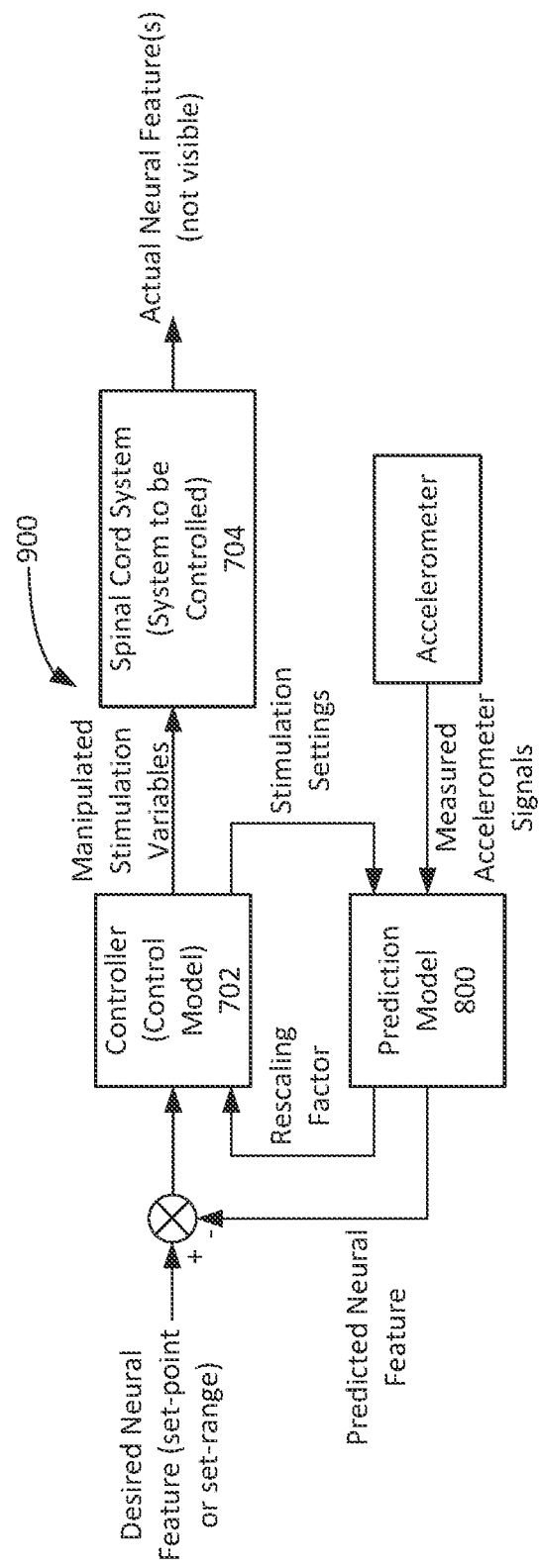
FIG. 9 shows a control system for using a predicted neural feature for controlling stimulation.

At step 614, a control system similar to the one described above (Step 606) can be used to adjust the stimulation settings to maintain the predicted neural feature within a set range and/or relative to a set-point. In other words, the predicted neural feature can be used as a feedback variable to maintain/adjust stimulation therapy or to prevent the neural feature to increase above a max-point (threshold). FIG. 9 illustrates a control system 900 configured to use predicted neural feature values determined from the prediction model 800 to maintain the estimated neural feature relative to a desired neural feature (i.e., a set-point, set-range, or threshold for the desired neural feature). Like the control system 700 described above, the control system 900 includes a controller (i.e., control model) 702, which may be a Kalman filtering algorithm, heuristic algorithm, simple threshold model, proportional-integral-derivative (PID) controller model, or the like. The measured accelerometer signals and stimulation parameters are fed into the prediction model 800, which determines one or more predicted neural features, as described above. The controller seeks to maintain the predicted neural feature relative to a set-point/set-range that has been determined to provide comfortable and effective therapy (i.e., a desired neural feature).

According to some embodiments, the feedback of the predicted neural feature determined by the prediction model 800 provided to the controller 702 may be rescaled to account for the lower stimulation intensity used during sub-perception stimulation. Recall from the discussion above, the prediction model was trained (during phase 1) using supra-perception stimulation, which has a greater intensity than the sub-perception used with the control system 900 (phase 2). The prediction model 800 may receive the stimulation settings as an input and may provide a scaling factor (based on the difference of stimulation intensity) to the controller to account for the difference in stimulation intensity.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method of treating pain in a patient using an implantable medical device (IMD) comprising an implantable pulse generator (IPG) configured for implantation in a patient and connectable to one or more electrode leads configured for implantation in the patient's spinal column, wherein each electrode lead comprises a plurality of electrodes, the method comprising:
   providing first stimulation to the patient's spinal cord using at least one of the plurality of electrodes;
   receiving one or more accelerometer signals from an accelerometer attached to the patient;
   correlating the one or more accelerometer signals with at least one feature of neural responses evoked in the patient's spinal cord by the first stimulation, wherein the at least one feature is indicative of pain treatment;
   providing second stimulation to the patient's spinal cord, wherein the second stimulation is configured to treat the patient's pain; and
   adjusting the second stimulation based on the correlation and the one or more accelerometer signals.

2. The method of claim 1, wherein the correlation and the one or more accelerometer signals is indicative of an orientation of the one or more electrode leads with respect to the patient's spinal cord.

3. The method of claim 1, wherein the correlation and the one or more accelerometer signals is indicative of a posture of the patient.

4. The method of claim 1, wherein the first stimulation is above a perception threshold of the patient.

5. The method of claim 4, wherein correlating the one or more accelerometer signals with at least one feature of neural responses:
   recording an electrospinogram (ESG) while providing the first stimulation and receiving the one or more accelerometer signals;
   processing the ESG to extract an evoked compound action potential (ECAP) signal from the ESG;
   determining one or more features of the ECAP signal; and
   correlating the one or more features of the ECAP signal with the one or more accelerometer signals.

6. The method of claim 5, wherein the correlating comprises determining a mathematical expression correlating the one or more features of the ECAP signal with the one or more accelerometer signals.

7. The method of claim 6, wherein the mathematical expression comprises a linear regression.

8. The method of claim 6, wherein the mathematical expression comprises a fitting algorithm selected from the group consisting of support vector machines (SVM), decision trees, and neural networks.

9. The method of claim 1, wherein the accelerometer is configured as a component of the IPG.

10. The method of claim 1, wherein the accelerometer is worn externally by the patient.

11. The method of claim 1, wherein the second stimulation is below a perception threshold of the patient.

12. The method of claim 1, wherein adjusting the second stimulation based on the correlation and the one or more accelerometer signals comprises maintaining the one or more accelerometer signals relative to a set-point.

13. The method of claim 1, wherein adjusting the second stimulation based on the correlation and the one or more accelerometer signals comprises using a control model to adjust stimulation settings.

14. The method of claim 13, wherein the control model is selected from the group consisting of Kalman filtering algorithms, heuristic algorithms, simple threshold model, and proportional-integral-derivative (PID) controller models.

15. An implantable medical device (IMD) comprising:
an implantable pulse generator (IPG) having a plurality of electrode nodes connectable to one or more electrode leads configured for implantation in the patient's spinal column, wherein each electrode lead comprises a plurality of electrodes, wherein the IPG is configured to:
provide first stimulation to the patient's spinal cord using at least one of the plurality of electrodes;
receive one or more accelerometer signals from an accelerometer attached to the patient;
correlate the one or more accelerometer signals with at least one feature of neural responses evoked in the patient's spinal cord by the first stimulation, wherein the at least one feature is indicative of pain treatment;
provide second stimulation to the patient's spinal cord, wherein the second stimulation is configured to treat the patient's pain; and
adjust the second stimulation based on the correlation and the one or more accelerometer signals.

16. The IPG of claim 15, wherein the correlation and the one or more accelerometer signals is indicative of an orientation of the one or more electrode leads with respect to the patient's spinal cord.

17. The IPG of claim 15, wherein the correlation and the one or more accelerometer signals is indicative of a posture of the patient.

18. The IPG of claim 15, wherein the first stimulation is above a perception threshold of the patient.

19. The IPG of claim 15, wherein the second stimulation is below a perception threshold of the patient.

20. The IPG of claim 15, wherein the accelerometer is configured as a component of the IPG.

* * * * *